United States Patent
Byrne et al.

(10) Patent No.: US 10,500,378 B2
(45) Date of Patent: Dec. 10, 2019

(54) MEDICAL BALLOON INCLUDING RADIOPAQUE INSERT FOR PRECISELY IDENTIFYING A WORKING SURFACE LOCATION

(71) Applicant: CLEARSTREAM TECHNOLOGIES LIMITED, Enniscorthy, County Wexford (IE)

(72) Inventors: Pat Byrne, Enniscorthy (IE); Angela Susan Crall, Tempe, AZ (US); Angela Kay Jensen, Tempe, AZ (US); Andrew Schaffer, Tempe, AZ (US); Sean Wall, Enniscorthy (IE)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 1038 days.

(21) Appl. No.: 14/383,760

(22) PCT Filed: Mar. 8, 2013

(86) PCT No.: PCT/US2013/029971
§ 371 (c)(1),
(2) Date: Sep. 8, 2014

(87) PCT Pub. No.: WO2013/134695
PCT Pub. Date: Sep. 12, 2013

(65) Prior Publication Data
US 2015/0112257 A1   Apr. 23, 2015

Related U.S. Application Data

(60) Provisional application No. 61/608,902, filed on Mar. 9, 2012.

(30) Foreign Application Priority Data

Mar. 9, 2012  (NL) .................................. 2008446

(51) Int. Cl.
*A61M 25/10* (2013.01)

(52) U.S. Cl.
CPC ....... *A61M 25/10* (2013.01); *A61M 2025/105* (2013.01); *A61M 2025/1079* (2013.01)

(58) Field of Classification Search
CPC .. A61M 2025/1079; A61M 2025/1081; A61M 2025/105; A61M 25/10;
(Continued)

(56) References Cited

U.S. PATENT DOCUMENTS

| | | | |
|---|---|---|---|
| 4,276,874 A | 7/1981 | Wolvek | |
| 4,292,974 A | 10/1981 | Fogarty | |

(Continued)

FOREIGN PATENT DOCUMENTS

| | | | |
|---|---|---|---|
| DE | 19952505 A1 | 5/2001 | |
| EP | 0850659 A1 | 7/1998 | |

(Continued)

*Primary Examiner* — Kami A Bosworth
(74) *Attorney, Agent, or Firm* — King & Schickli, PLLC

(57) ABSTRACT

A balloon catheter adapted for use with a guidewire includes an elongated, tubular shaft extending in a longitudinal direction, said shaft having a proximal end and a distal end. An inflatable balloon is supported along the distal end of the shaft, the balloon when inflated including first and second spaced ends and a working surface between the ends. An insert located within the interior compartment of the balloon includes at least a radiopaque portion separate from the shaft. Related methods are also disclosed.

9 Claims, 13 Drawing Sheets

(58) Field of Classification Search
CPC .......... A61M 25/1009; A61M 25/1038; A61M 25/104; A61M 2025/1004; A61M 2025/1047; A61M 2025/1059; A61M 2025/1068; A61M 2025/1075; A61M 2025/1084; A61M 2025/1043
See application file for complete search history.

(56) References Cited

U.S. PATENT DOCUMENTS

| | | | |
|---|---|---|---|
| 4,994,032 A | 2/1991 | Sugiyama et al. | |
| 5,085,636 A | 2/1992 | Burns | |
| 5,102,402 A * | 4/1992 | Dror | A61F 2/958 604/103.02 |
| 5,209,730 A | 5/1993 | Sullivan | |
| 5,549,552 A * | 8/1996 | Peters | A61M 25/1034 604/103.1 |
| 5,709,661 A | 1/1998 | Van Egmond et al. | |
| 5,779,731 A * | 7/1998 | Leavitt | A61M 25/0108 604/103.1 |
| 5,851,210 A | 12/1998 | Torossian | |
| 5,860,923 A | 1/1999 | Lenker et al. | |
| 5,865,721 A * | 2/1999 | Andrews | A61M 25/1029 600/18 |
| 5,968,069 A * | 10/1999 | Dusbabek | A61F 2/958 604/96.01 |
| 6,004,289 A | 12/1999 | Saab | |
| 6,123,718 A * | 9/2000 | Tu | A61B 18/1492 606/41 |
| 6,425,882 B1 * | 7/2002 | Vigil | A61M 25/10 604/103.14 |
| 6,520,934 B1 | 2/2003 | Lee | |
| 6,540,721 B1 | 4/2003 | Voyles | |
| 6,638,294 B1 * | 10/2003 | Palmer | A61F 2/013 606/200 |
| 6,746,425 B1 | 6/2004 | Beckham | |
| 6,884,234 B2 | 4/2005 | Aita et al. | |
| 6,884,257 B1 | 4/2005 | Cox | |
| 7,520,876 B2 | 4/2009 | Ressemann et al. | |
| 8,685,074 B2 | 4/2014 | Eidenschink et al. | |
| 2002/0198559 A1 | 12/2002 | Mistery | |
| 2003/0014007 A1 * | 1/2003 | Eidenschink | A61M 25/104 604/96.01 |
| 2004/0236366 A1 | 11/2004 | Kennedy | |
| 2004/0243156 A1 | 12/2004 | Wu et al. | |
| 2006/0079836 A1 * | 4/2006 | Holman | A61M 25/10 604/96.01 |
| 2006/0085022 A1 | 4/2006 | Hayes et al. | |
| 2006/0085023 A1 | 4/2006 | Davies et al. | |
| 2006/0085024 A1 | 4/2006 | Pepper et al. | |
| 2006/0224114 A1 | 10/2006 | Van Sloten | |
| 2006/0287665 A1 | 12/2006 | Burton | |
| 2007/0005092 A1 * | 1/2007 | Godin | A61M 25/0023 606/194 |
| 2007/0100280 A1 | 5/2007 | Van Sloten | |
| 2007/0142771 A1 | 6/2007 | Durcan | |
| 2008/0045896 A1 | 2/2008 | Yribarren et al. | |
| 2008/0188803 A1 | 8/2008 | Jang | |
| 2008/0228138 A1 | 9/2008 | Van Sloten | |
| 2008/0249464 A1 * | 10/2008 | Spencer | A61M 25/1002 604/103 |
| 2009/0018500 A1 | 1/2009 | Carter | |
| 2009/0018501 A1 * | 1/2009 | Yribarren | A61M 25/0119 604/103.01 |
| 2009/0024087 A1 | 1/2009 | Kennedy | |
| 2009/0036829 A1 | 2/2009 | Pagel | |
| 2009/0171278 A1 | 7/2009 | Hirszowicz | |
| 2011/0004057 A1 | 1/2011 | Goldfarb | |
| 2011/0029048 A1 | 2/2011 | Mahrouche | |
| 2011/0196296 A1 * | 8/2011 | Rickert | A61M 25/10 604/96.01 |
| 2011/0230700 A1 | 9/2011 | Sing et al. | |
| 2012/0232528 A1 | 9/2012 | Eli et al. | |

FOREIGN PATENT DOCUMENTS

| | | |
|---|---|---|
| GB | 2355797 A | 5/2001 |
| JP | H09327515 A | 12/1997 |
| JP | 2007020885 A | 2/2007 |
| WO | 8800844 A1 | 2/1988 |
| WO | 9619256 A1 | 6/1996 |
| WO | 9912601 A1 | 3/1999 |
| WO | 0057816 A1 | 10/2000 |
| WO | 2005096797 A1 | 10/2005 |
| WO | 2005107646 A1 | 11/2005 |
| WO | 2006135581 A2 | 12/2006 |
| WO | 2007054364 A2 | 5/2007 |
| WO | 2007094374 A1 | 8/2007 |
| WO | 2007132447 A2 | 11/2007 |
| WO | 2010003135 A2 | 1/2010 |
| WO | 2010051488 A1 | 5/2010 |
| WO | 2013132070 A2 | 9/2013 |
| WO | 2013132071 A1 | 9/2013 |
| WO | 2013134688 A2 | 9/2013 |
| WO | 2013134691 A1 | 9/2013 |
| WO | 2013134695 A1 | 9/2013 |
| WO | 2013134696 A1 | 9/2013 |
| WO | 2013134697 A1 | 9/2013 |
| WO | 2013134701 A2 | 9/2013 |
| WO | 2013134702 A1 | 9/2013 |
| WO | 2013134704 A1 | 9/2013 |
| WO | 2013134708 A1 | 9/2013 |

* cited by examiner

MEDICAL BALLOON INCLUDING RADIOPAQUE INSERT FOR PRECISELY IDENTIFYING A WORKING SURFACE LOCATION

The following U.S. Provisional Patent Applications are incorporated by reference: 61/608,852; 61/608,859; 61/608,862; 61/608,897; 61/608,902; 61/608,908; 61/608,913; 61/608,917; 61/608,927; 61/608,932; 61/608,941; and 61/747,444.

TECHNICAL FIELD

This disclosure relates generally to balloons for performing medical procedures, such as angioplasty and, more particularly, to a medical balloon having a predetermined portion, such as a working surface, that may be precisely located or identified during use.

BACKGROUND OF THE INVENTION

Balloons are routinely used to resolve or address flow restrictions or perhaps even complete blockages in tubular areas of the body, such as arteries or veins. In many clinical situations, the restrictions are caused by hard solids, such as calcified plaque, and require the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

In clinical practice, angioplasty balloons are expanded from a deflated, folded state to an expanded state within a vessel to treat a target area, such as a portion of the circumferential inner wall I of a blood vessel V, as shown in FIGS. 1 and 2. The inflation of a balloon 12 with wall 28 is traditionally completed using an X-ray contrast agent CM along dimension DX to provide better visibility under X-ray or other form of radiography R during the interventional procedure, as illustrated in FIGS. 3 and 3a (which shows the intensity measured by a fluoroscope detector plate, FDP). Typically, a 70/30 percent mixture of contrast agent and saline is used to inflate the balloon during an angioplasty procedure.

In general, a desirable goal is to reduce inflation and deflation times required for balloons without sacrificing the profile of the balloons, especially for large volume balloons (which can require up to two minutes of inflation/deflation times with the contrast agent). Because of its relatively high viscosity, it would also be desirable to eliminate, or at least reduce the amount of, the contrast agent used in inflation/deflation of the balloons. The use of contrast agent prolongs the inflation/deflation times and also poses the risk of iodine exposure to patients sensitive to iodine. In this regard, a non-radiopaque substance could be used in lieu of the contrast agent, such as for example saline or carbon dioxide, but such substances are invisible during X-ray imaging, and thus do not enhance visibility.

Furthermore, the physician performing the angioplasty procedure should be able to locate the position of the uninflated balloon with accuracy, so that the balloon will be properly positioned once inflated. This is conventionally accomplished by attaching marker bands on the catheter shaft in the region corresponding to the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

Misalignment of the marker bands during placement along the shaft sometimes results in their failure to correspond precisely to the extent of the working surface, as is shown in FIG. 4 (note misalignment amount X between each interior marker band M carried by shaft S and working surface W of balloon 12, which also typically includes a radiopaque tip P at the distal end). Even upon exercising great care to position the markers properly on the underlying shaft in alignment with anticipated boundaries of the working surface when the balloon is inflated, there remains a tendency for mismatch due to several possible factors. One such factor may be the tolerance stack-ups arising as a consequence of the affixation of the balloon to the distal end of the catheter shaft. The balloon also has a tendency to grow in the longitudinal direction when inflated, especially with large and particularly long balloons. Another factor is the tendency of the portion of the catheter shaft within the balloon to bend or flex during inflation. This may lead to misalignment between radiopaque markers fixed to the shaft and the working surface.

Whatever the cause, the resulting misalignment may prevent the clinician from accurately identifying the location of the working surface of the balloon during an interventional procedure. This may lead to a geographic misplacement, or "miss," of the intended contact between the target area T and the working surface W of the balloon 12 (see FIG. 2). It is especially desirable to avoid such an outcome when the balloon is designed to deliver a payload (such as a drug, stent, or both) or a working element to a specified location within the vasculature, since a miss may prolong the procedure (such as, for example, by requiring redeployment of the balloon 12 or the use of another balloon catheter in the case of a drug coated balloon).

Upon deflation, the balloon may also be subject to a phenomenon known as "pancaking." In this condition, the balloon 12 folds down upon itself to a flattened state, as shown in FIG. 5. This situation may cause the balloon to be viewed through fluoroscopy as perhaps still being in the inflated condition, since the full width of the balloon may be perceived in the flattened state. This can give the clinician the false perception that the balloon remains inflated, when in fact it is not.

Accordingly, the need is identified for a balloon for which the working surface may be identified during an interventional procedure with enhanced precision. The solution would take into account the possible mismatch between fixed locations on the catheter shaft and the balloon to define the working surface, and would operate independent of the position of the portion of the catheter shaft within the balloon. The improved identification may also allow for the better detection of the false perception of deflation caused by pancaking. Overall, procedural efficiency would be enhanced without remarkably increasing cost or complexity, and in a manner that can be applied to many existing catheter technologies without extensive modification.

SUMMARY OF THE INVENTION

An object of the disclosure is to provide a balloon for which the working surface may be identified during an interventional procedure with enhanced precision.

MODES FOR CARRYING OUT THE INVENTION

The description provided below and in regard to the figures applies to all embodiments unless noted otherwise, and features common to each embodiment are similarly shown and numbered.

Figure 1:
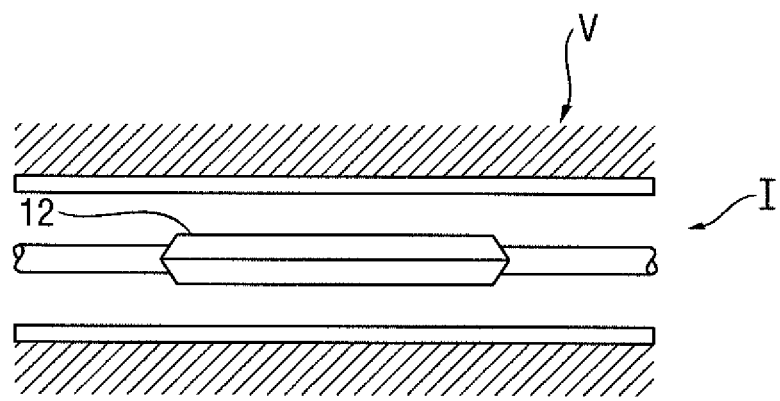
FIGS. 1-9 are illustrative of the background of the invention.
Figure 2:
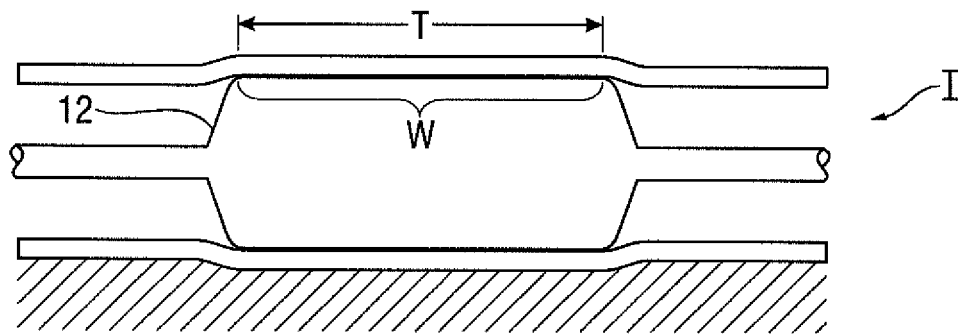
Figure 3:
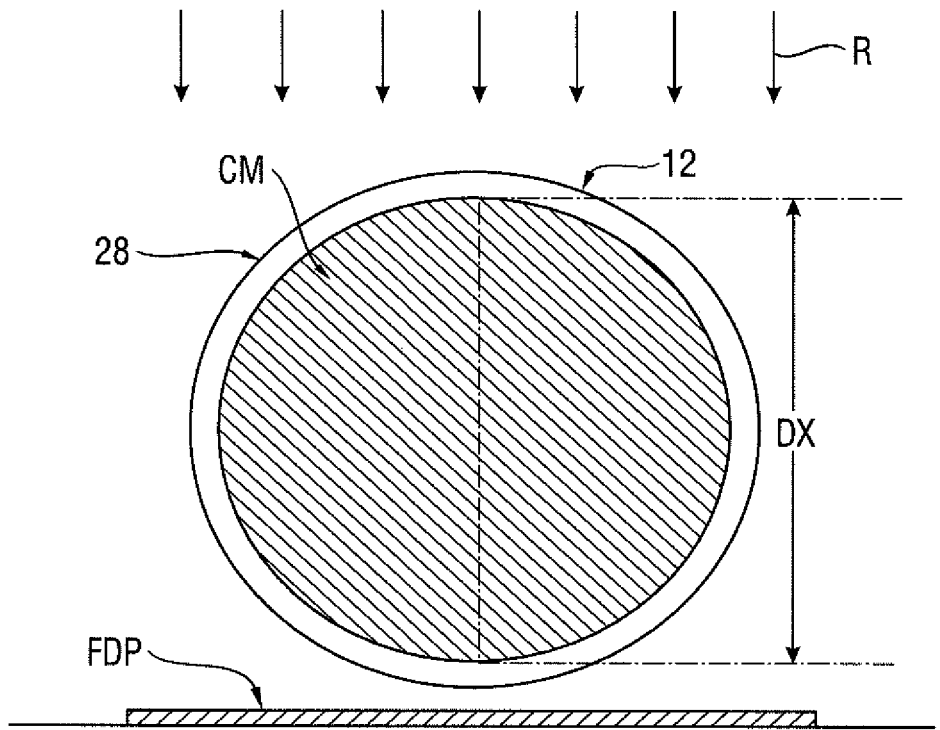
Figure 3A:
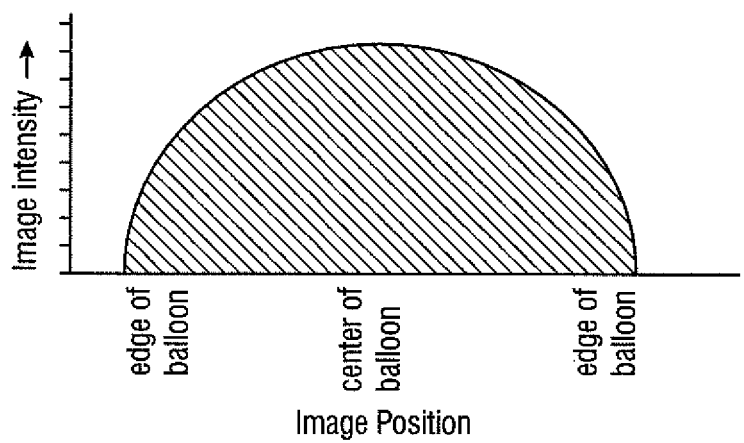
Figure 4:
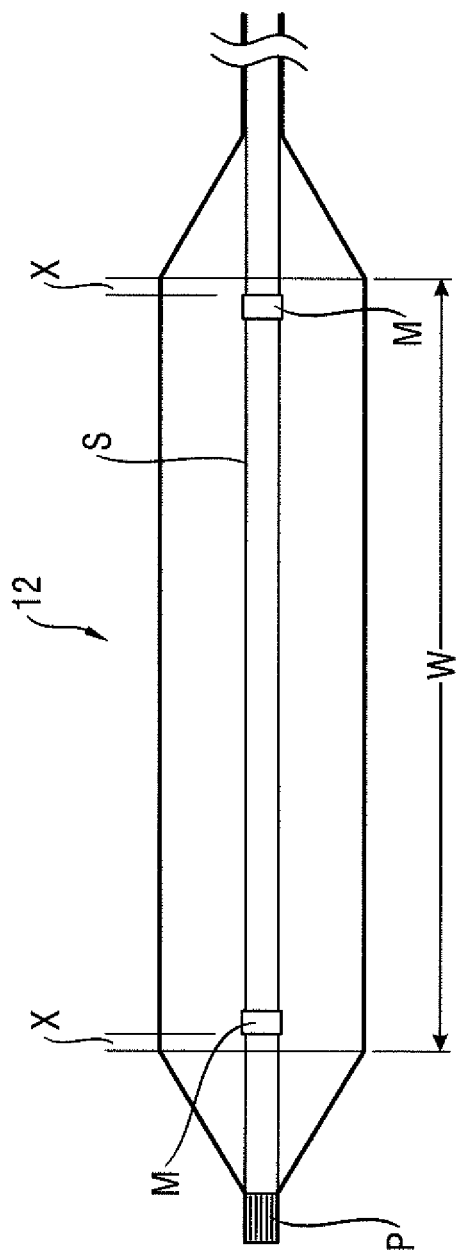
Figure 5:
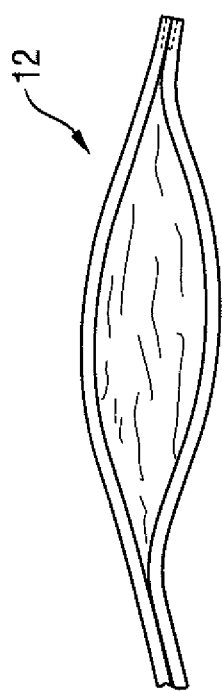
Figure 6:
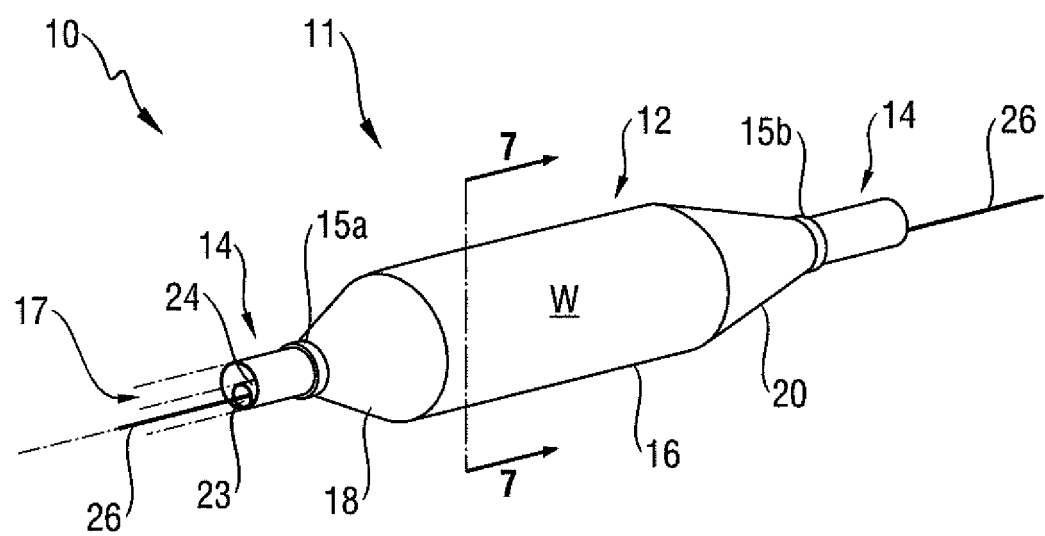
Figure 7:
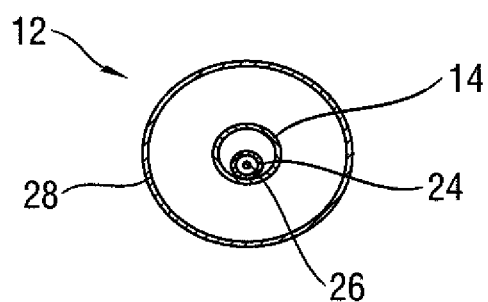
Figure 8:
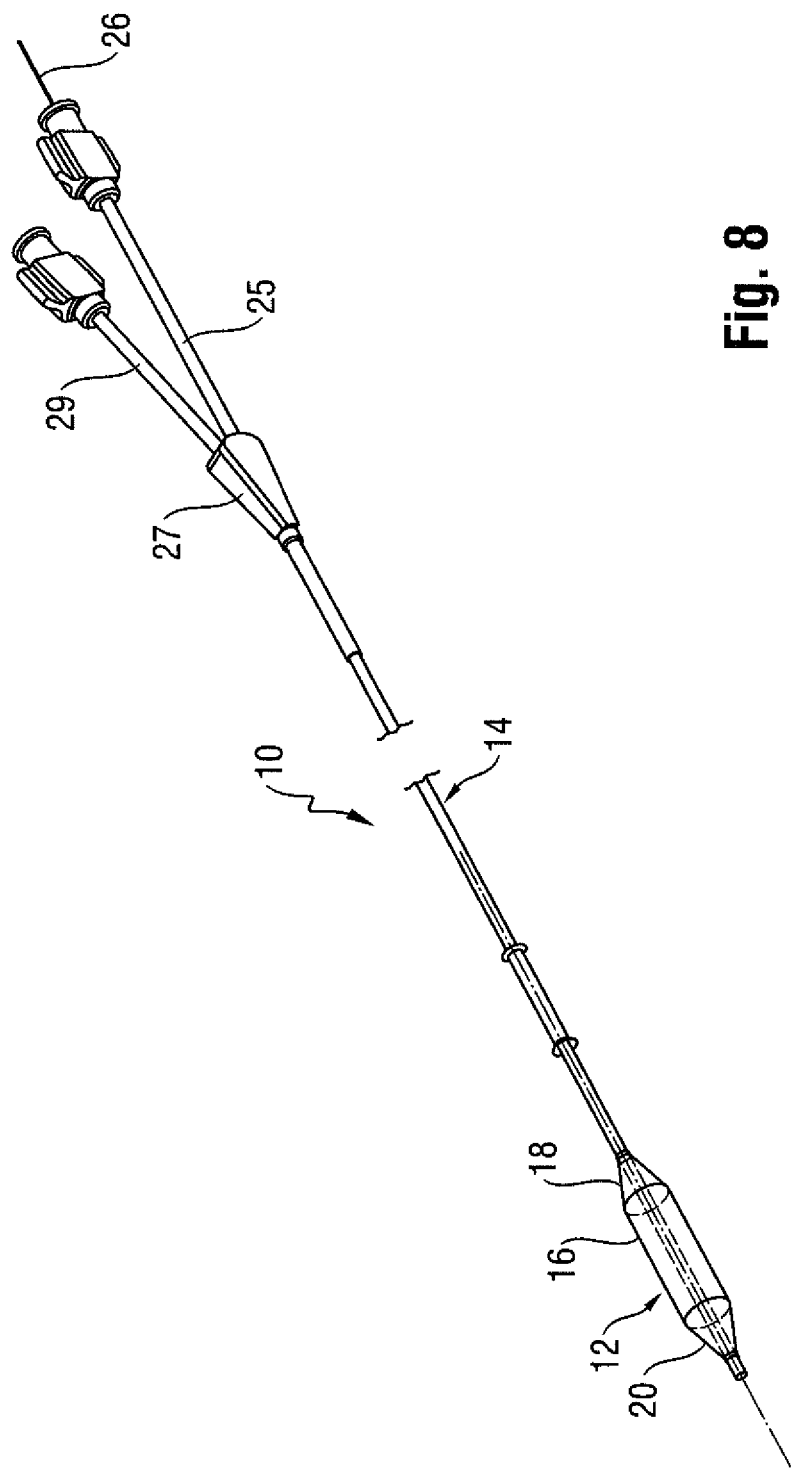

Provided is a catheter 10 having a distal portion 11 with a balloon 12 mounted on a catheter tube 14. Referring to FIGS. 6, 7, and 8, the balloon 12 has an intermediate section 16, or "barrel," and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed at balloon ends (proximal end 15a and distal end 15b) on the cone sections 18, 20 to allow the inflation of the balloon 12 via one or more inflation lumens 17 extending within catheter tube 14 and communicating with the interior of the balloon 12.

Figure 9:
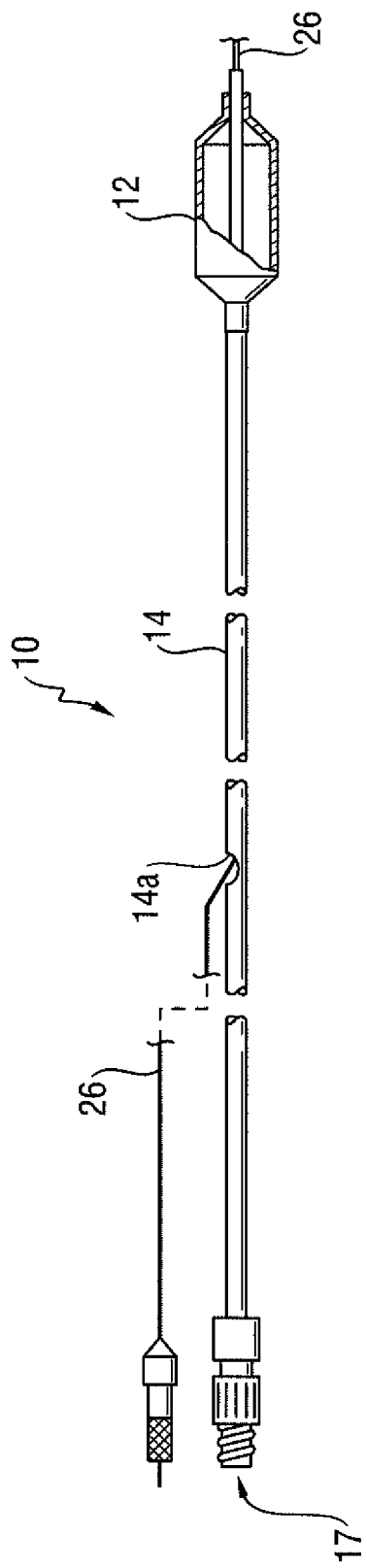

The catheter tube 14 also includes an elongated, tubular shaft 24 forming a guidewire lumen 23 that directs the guidewire 26 through the catheter 10, and along the distal end of which the balloon 12 may be located. As illustrated in FIG. 8, this guidewire 26 may extend through the proximal end of the catheter 10 and a first port 25 of a connector 27 into the lumen 23 to achieve an "over the wire" (OTW) arrangement, but could also be provided in a "rapid exchange" (RX) configuration, in which the guidewire 26 exits a lateral opening 14a closer to the distal end (see FIG. 9) or else is fed through a passage associated with the tip P distally of the balloon 12 ("short" RX; not shown). A second port 29 may also be associated with catheter 10, such as by way of connector 27, for introducing a fluid (e.g., saline, a contrast agent, or both) into the interior compartment of the balloon 12 via the inflation lumen 17.

Balloon 12 may include a single or multi-layered balloon wall 28 forming the interior for receiving the inflation fluid. The balloon 12 may be a non-compliant balloon having a balloon wall 28 that maintains its size and shape in one or more directions when the balloon is inflated. Examples of non-compliant balloons may be found in U.S. Pat. No. 6,746,425 and Publication Nos. US 2006/0085022, US 2006/0085023 and US 2006/0085024, the disclosures of which are hereby incorporated herein by reference. The balloon 12 in such case also has a pre-determined surface area that remains constant during and after inflation, also has a pre-determined length and pre-determined diameter that each, or together, remain constant during and after inflation. However, the balloon 12 could be semi-compliant or compliant instead, depending on the particular use.

In order to provide an enhanced locatability during an interventional procedure, the balloon 12 may have a radiopaque quality. In one embodiment, this radiopaque quality is provided in a manner that allows for a clinician to differentiate, with relative ease and high precision, one portion of the balloon 12 from another (such as the barrel section 16 including the working surface W from the cone sections 18, 20). This helps the clinician ensure the accurate positioning of the balloon 12 and, in particular, the working surface W, at a specified treatment location, which may be especially important in the delivery of drugs via the balloon surface, as outlined in more detail in the following description.

Figure 11:
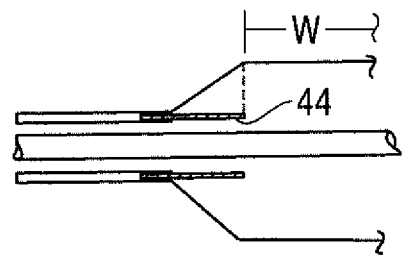
Figure 10:
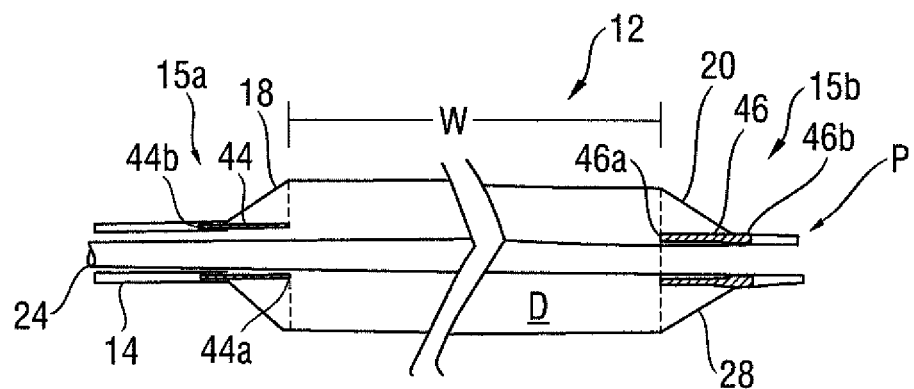
FIG. 10 illustrates a first embodiment according to the disclosure.

One manner of providing an identification of a particular segment of a balloon 12, such as the working surface W, is described with reference to FIGS. 10, 11 and 12. In this embodiment, at least one insert 44 having a radiopaque quality is provided within the interior compartment of the balloon 12. Although contact may be made in the folded condition of the balloon 12 or otherwise, the insert 44 is separate from (i.e., not connected to) the shaft 24, and generally spaced from the wall 28 forming the proximal cone section 18.

This insert 44 may be tubular in form, and extend in a spaced apart manner along and generally coaxially with the shaft 24 extending through the interior compartment. A free end portion 44a of the insert 44 is located at a position aligned with the edge or extent of the working surface W at the proximal end 15a, while the opposite, fixed end portion 44b is connected to the balloon 12, such as at the point where it attaches to the tube 14 at the proximal end. The connection between the insert 44 and the balloon 12, tube 14, or both, may be by way of interference fit, bonding (using an adhesive, welding, etc.), friction, or other like manners of forming a secure arrangement that does not permit relative movement of two distinct parts when connected.

In use, this allows for the accurate identification of the proximal edge of the working surface W independent of the position of the inner member (e.g., shaft 24), given that the insert 44 is not intimately attached to it. In other words, any flexing or misalignment of the shaft 24 has no bearing on whether the radiopaque end 44a of the insert 44 aligns with the proximal edge of the working surface W. A more precise alignment between the radiopaque identifier and the edge of the working surface W may thus result, with the advantage that a geographic miss may be less likely.

Figure 11A:
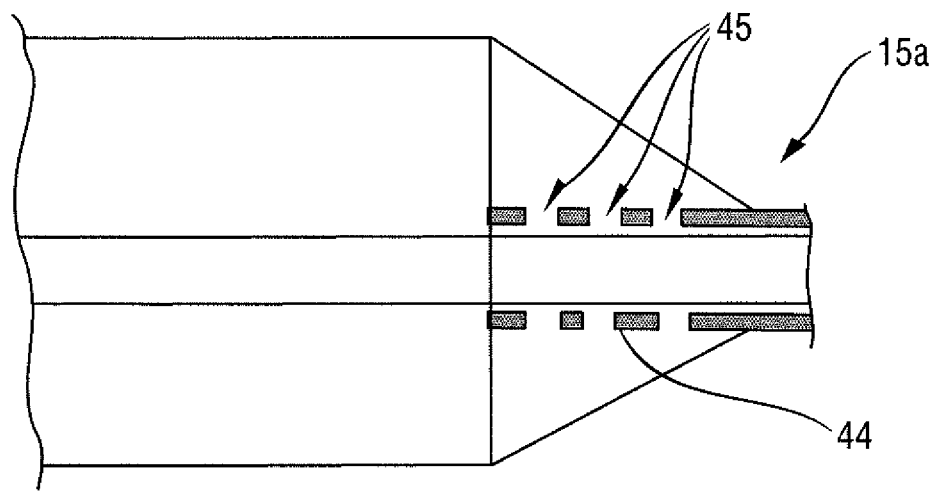
FIGS. 11a and 12a illustrate other embodiments according to the disclosure.

One or both of the inserts 44 or 46 may also be adapted so as to minimize interference with the balloon wall 28 during inflation of the balloon 12. For example, as shown in FIG. 11a, the insert 44 may be provided with one or more perforations 45. These perforations 45 may serve several functions. For example, the perforations 45 may prevent the balloon wall 28 from sticking to the insert outer wall, such as the result of a vacuum. Similar perforations may be provided on insert 46 (not shown). Also, the perforations 45 prevent the insert 44 from serving as a barrier that would retard the inflation fluid emanating from the tube 14 from readily flowing into the interior compartment of the balloon 12, and thus help to preserve the desired short inflation times. Indeed, the presence of such perforations 45 may allow the inserts 44 and 46 to be combined into a single unitary piece of material extending continuously between the proximal and distal ends 15a, 15b of the balloon 12.

Figure 12:
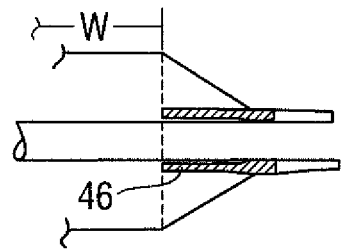
FIGS. 11 and 12 are partial views of the FIG. 10 embodiment.
Figure 12A:
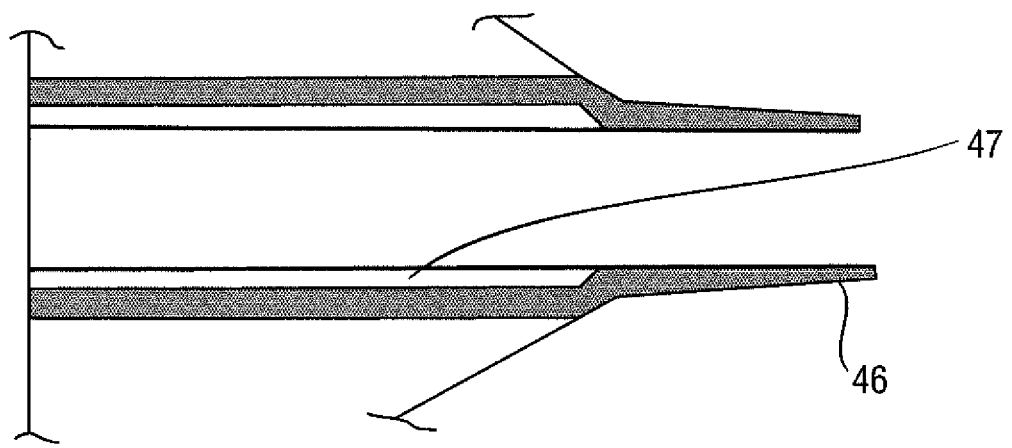

Turning back to FIG. 10 and referencing FIG. 12 as well, a second, at least partially radiopaque insert 46 may also be provided at the distal end 15b including the conical section 20. In one embodiment, this insert 46 is arranged at the location where the distal end 15*b* of the balloon 12 is secured to the shaft 24 to form the tip P (which as noted may also be radiopaque). As shown in FIG. 12*a*, this insert 46 may be connected to the shaft 24, or may be embedded within the material forming the corresponding distal end 15*b* of the balloon 12 (especially if a multi-layered arrangement is used to form the balloon wall 28).

In any case, the proximal end portion 46*a* of the insert 46 terminates at the distal edge of the working surface W, so as to assist in the identification process. The proximal end portion 46*a* of this insert 46 extending within the interior compartment of the balloon 12 may be spaced from the shaft 24 (note gap 47 in FIG. 12*a*) so as to be less susceptible to any misalignment caused by bending. This end 46*a* may be partially or entirely radiopaque. This radiopaque end portion 46*a* provides an indication of the distance between the distal edge of the working surface W and the distal end 15*b* of the balloon 12. Also, the distal end portion 46*b* of the insert 46 may be formed with the tip P as a unitary, continuously radiopaque structure (for example, with different radiopaque qualities (patterns, shapes, densities, etc.)), if desired to allow for ready identification of these components.

Figure 13:
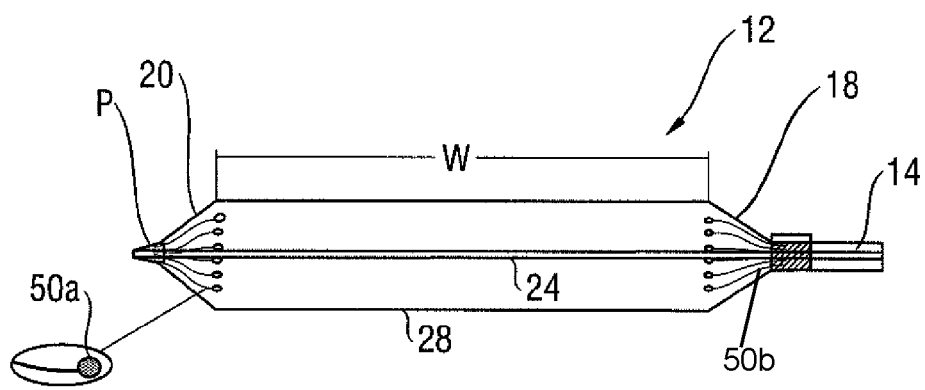
FIGS. 13 and 14 illustrate a further embodiment according to the disclosure.
Figure 14:
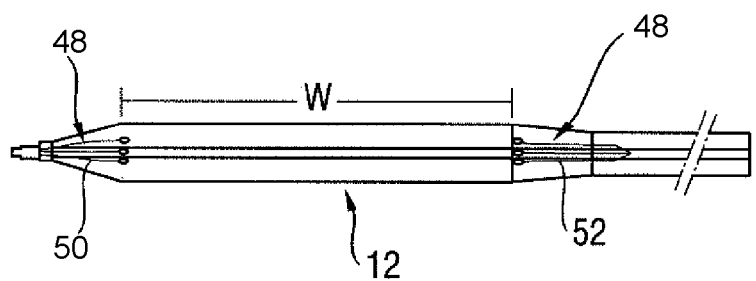

A further embodiment is shown in FIGS. 13 and 14, in which a second type of insert 48 is provided. This insert 48 may include one or more portions in the form of struts or fingers projecting within the interior compartment of the balloon 12 and at least partially separate from the shaft 24. The struts or fingers may take the form of individual elongated wires 50 arranged in an umbrella-like configuration, and partially or completely formed of a radiopaque material.

Specifically, in one embodiment, one or more of the wires 50 includes a radiopaque end portion 50*a* corresponding to the junction defining the working surface W of the balloon 12 at the proximal or distal ends, or both. The end portion 50*a* of one or more of the wires 50 may be fabricated of a metal or polymer material, and may also be formed in an oversized manner relative to the remainder of the wire. For example, the wire 50 may have a generally circular cross-section, with the end portions 50*a* comprising pads, beads, spheres, discs, or the like, each having a greater diameter than the circular cross-section of the supporting wire. In any case, the spaced apart nature of the wires 50 and their relatively narrow construction helps to avoid delayed inflation times, as the inflation fluid may freely flow past the fingers into the interior compartment.

In one embodiment, the one or more wires 50 may be adhered to an interior surface of the balloon wall 28 at the edges of the working surface W, such as for example by bonding end portion 50*a*. This may help to ensure the proper relative positioning in both the inflated and deflated conditions of the balloon 12. In any case where the radiopacity is provided at the end portion 50*a* of the wire 50 aligned with the edges of the working surface W, it should be appreciated that the remainder may be fabricated of a material lacking any enhanced radiopacity (e.g., a polymer that does not include a radiopaque additive, coating, etc.).

The wires 50 at a fixed end portion 50*b* opposite the free end portion 50*a* may be attached to the balloon 12 at the proximal and distal ends 15*a*, 15*b* where the bond or seal is formed, thus separating them from any inner member (e.g., shaft 24). In one possible embodiment, the wires 50 are flexible, and thus may be nominally collapsed when the balloon 12 is in a folded condition (FIG. 14), and then allowed to expand on inflation. However, it can be appreciated that in both the inflated and deflated conditions, the end portions 50*a* of the wires 50 may remain aligned with the proximal and distal boundaries of the working surface W, respectively, and thus help to assure the correct positioning prior to inflation and thereafter.

To ensure the wires 50 perform as intended, they could be fabricated of a material having a shape memory (e.g., NITINOL). Such a material may allow for an ambient condition, such as temperature, to be used to ensure the expanded or retracted condition is reliably achieved. The wire 50 may thus be designed to have an initial shape (e.g., flat) and then assume a different shape corresponding to that for identifying the working surface W of the balloon 12 in the inflated condition based on a variation in temperature (such as that resulting from the contrast fluid when introduced into the interior compartment of the balloon 12). In such case, the radiopaque portion or portions may be designed to align in a more precise fashion with the working surface W, as compared to conventional marker bands swaged to the shaft 24 passing through the interior compartment of the balloon 12.

Additionally or alternatively, a retractable sheath 52 could be provided for selectively retracting and allowing the wires 50 to move to the expanded condition on inflation. The sheath 52 could be operated by the clinician using a remote mechanism, or could be arranged to be pressure activated on inflation (e.g., a pressure of 1 bar causes retraction and allows the wires 50 to expand, and a lesser (or no) pressure reverses the operation).

Figure 15:
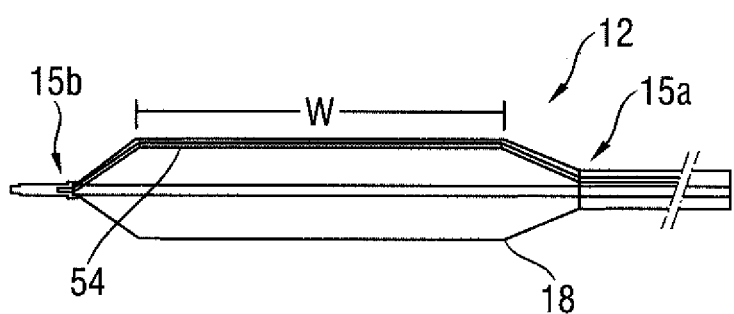
FIGS. 15-17 illustrates yet another embodiment according to the disclosure.
Figure 16:
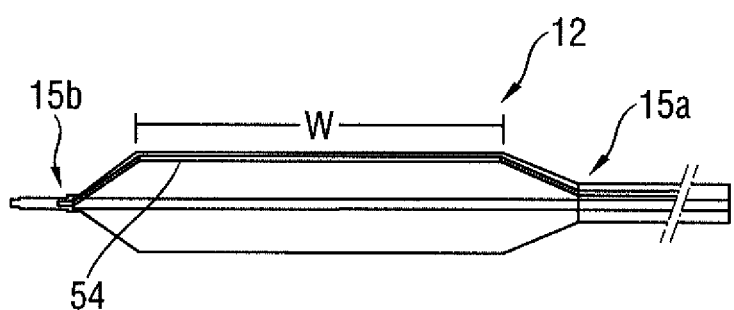

A further embodiment of a radiopaque insert is shown in FIG. 15, which comprises an at least partially radiopaque wire 54 extending within the interior compartment of the balloon 12 from the proximal end 15*a* to the distal end 15*b*. The ends of the wire 54 may be included in the bond forming the seal between the tube 14 and the balloon proximal end 15*a*, and the tip O and the balloon distal end 15*b*. The radiopaque portion of the wire 54 may correspond to the barrel section 16 including the working surface W, as shown in FIG. 15, or may correspond to one or both of the end sections 18, 20, as shown in FIG. 16.

Figure 17:
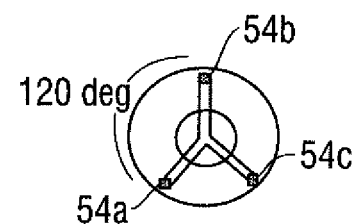
Figure 18:
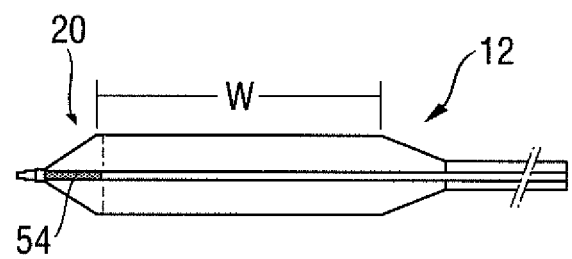
FIGS. 18-20 illustrates still a further embodiment according to the disclosure.
Figure 19:
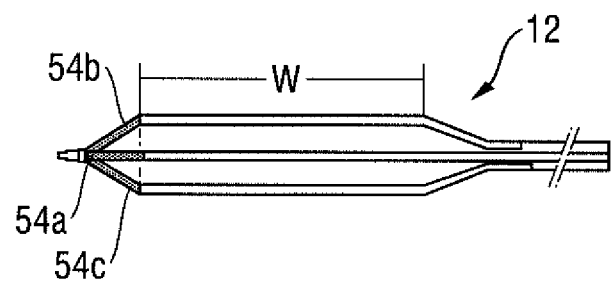
Figure 20:

As with the other embodiments, more than one insert in the form of a wire 54 may also be provided. For example, as shown in FIG. 17, three wires 54*a*, 54*b*, 54*c* spaced equidistantly around the circumference of the balloon 12 may be provided, but two, four, or more wires could be provided, and need not be spaced equally apart. Also, only a single portion of any wire 54 may be radiopaque, as shown in FIG. 18 as corresponding to distal cone section 20 of balloon 12. In any case, the presence of multiple wires, especially when having a radiopaque portion extending along the cones, as shown in FIG. 19, may help to distinguish between the flattened or pancaked condition, as the appearance of the balloon 12 when deflated would appear remarkably different than in the inflated condition, as can be seen in balloon 12' in FIG. 20.

Figure 21:
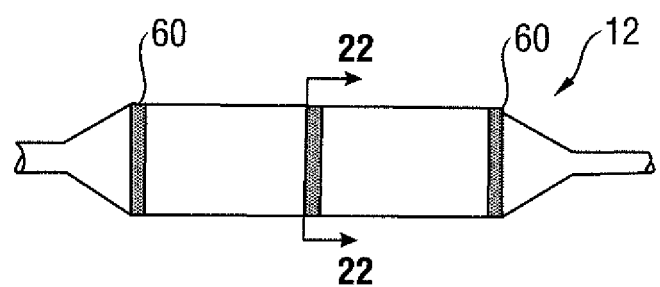
FIG. 21 illustrates another embodiment according to the disclosure.
Figure 22:
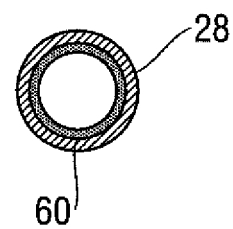
FIG. 22 is a cross-sectional view taken along line 22-22 of FIG. 21.

The radiopaque identifier may take the form of one or more radiopaque bands 60 inserted in the interior compartment of the balloon 12. In one embodiment, as shown in FIG. 21 and the related cross-sectional view of FIG. 22, the bands 60 are positioned along the inner surface of the balloon wall 28, with one at each edge of the working surface W. A band 60 may also be provided along the working surface W, so as to help confirm the full inflation of the balloon 12 under fluoroscopy. The one or more bands 60 may be formed from a compliant or elastic material so as to stretch along with the balloon when moving between the deflated and inflated states, and may be a metal (including possibly a shape memory material, such as NITINOL, to change shape based on an ambient factor, such as an increase or decrease in temperature) or a polymer material. The bands 60 may be inserted into the interior compartment of the balloon 12 prior to folding, or may be provided on the shaft 24 and bonded to the balloon 12 when folded (and then expanded along with the balloon wall 28 upon inflation).

The bands 60 may also comprise a radiopaque material applied to the interior surface of the balloon wall 28, such as by painting or other bonding. In one example, the radiopaque material comprises gold applied to the interior surface of the balloon 12, such as in the form of a band 60. The gold may be applied in leaf form, given its softness and malleability, which also means that it will not in any way hinder the expansion of the balloon 12.

Any of the inserts described above may also be used in connection with other radiopaque identifiers, such as patterns, bands, strips or the like. Details may be found in co-pending applications filed on the same date as this application, entitled "MEDICAL BALLOON WITH RADIOPAQUE IDENTIFIER FOR PRECISELY IDENTIFYING THE WORKING SURFACE," for inventors Sean Wall, Pat Byrne, Robert Righi, Angela Crall, Paul Wales, and Allan Ronan, and "MEDICAL BALLOON WITH RADIOPAQUE END PORTION FOR PRECISELY IDENTIFYING A WORKING SURFACE LOCATION," for inventors Sean Wall, Scott Randall, Robert Righi, and Angela Crall. The disclosures of the foregoing applications are herein incorporated by reference.

Balloons 12 that carry one or more surface elements, such as a payload (drug, stent, or both) or a working implement (cutter, focused force wire, or the like) into the vasculature may also benefit from the foregoing description of marking techniques. For example, as shown in FIG. 10, a balloon 12 including a defined working surface W, such as by providing radiopaque markings 30 at the transitions between the barrel section 16 and cone sections 18, 20, may include a portion coated with such a drug D, such as one designed for achieving a desired therapeutic effect when applied to the interior of the vessel. The radiopaque marking 30 may also correspond to the location of the drug D on the balloon 12, such as along the entire working surface W or only a portion of it. The drug D may be applied to the inflated balloon as part of the manufacturing process, and prior to folding for insertion in the vasculature. The clinician may thus with the benefit of a fluoroscope determine the precise positioning of the working surface W prior to inflating the balloon 12 in the vasculature to deliver the drug D to the desired location and provide the desired treatment regimen.

Examples of suitable radiopaque materials include, but are not limited to, barium, bismuth, tungsten, iridium, iodine, gold, iron, or platinum. The amounts used may vary depending on the desired coverage and the desired degree of radiopacity.

The subject matter of each of the paragraphs below citing a balloon or a catheter can be part of a balloon or a catheter respectively that is cited in any of the other paragraphs:

1.1 A balloon catheter, comprising: an elongated, tubular shaft extending in a longitudinal direction, said shaft having a proximal end and a distal end; and an inflatable balloon supported along the distal end of the shaft, the balloon when inflated including first and second spaced conical end sections and a working surface between the conical sections, the balloon further including at least one radiopaque marking identifying the transition from the conical end section to the working surface.

1.2 The catheter of paragraph 1.1, wherein the at least one radiopaque marking comprises a first radiopaque marking at a first transition between the first conical end section and the working surface, and further including a second radiopaque marking at a second transition between the second conical end section and the working surface.

1.3 The catheter of any of the foregoing paragraphs, wherein the at least one marking comprises a strip.

1.4 The catheter of any of the foregoing paragraphs, further including a plurality of radiopaque markings in the form of strips.

1.5 The catheter of paragraph 1.4, wherein the strips extend at least partially in a longitudinal direction between the first and second conical end sections.

1.6 The catheter of paragraphs 1.4 or 1.5, wherein the strips comprise annular bands.

1.7 The catheter of any of the foregoing paragraphs, wherein at least two spaced radiopaque markings are provided on each conical end section, including one adjacent a distal portion and a proximal portion of each conical end section.

1.8 The catheter of any of the foregoing paragraphs, wherein the balloon includes a barrel section between the first and second conical end sections, and further including a plurality of radiopaque markings on the barrel section.

1.9 The catheter of any of the foregoing paragraphs, wherein the marking comprises a first pattern on the conical end sections and further including a second, different pattern on the working surface.

1.10 The catheter of any of the foregoing paragraphs, wherein the at least one marking is selected from the group consisting of a pattern, a strip, a brand, a logo, a letter, a number, a word, or combinations thereof.

1.11 The catheter of any of the foregoing paragraphs, wherein the identifier comprises a scale.

1.12 The catheter of any of the foregoing paragraphs, wherein the balloon includes a drug.

1.13 The catheter of paragraph 1.12, wherein the drug corresponds to the location of the radiopaque marking.

1.14 The catheter of paragraph 1.12, wherein the drug corresponds to other than the location of the radiopaque marking.

1.15 The catheter of paragraph 1.12, wherein the radiopaque marking comprises the drug formulated to include a radiopacifier.

1.16 A balloon having a drug carried on a working surface of the balloon wall and a radiopaque identifier identifying the location of the drug on the balloon.

1.17 The balloon of paragraph 1.16, wherein the radiopaque identifier comprises a radiopaque material mixed with a formulation comprising the drug.

1.18 The balloon of paragraph 1.16, wherein the working surface is along a barrel section of the balloon, and the radiopaque identifier is on one or both cone sections of the balloon.

2.1 A balloon catheter, comprising: an elongated, tubular shaft extending in a longitudinal direction, said shaft having a proximal end and a distal end; and an inflatable balloon supported along the distal end of the shaft, the balloon when inflated including a generally cylindrical barrel section forming a working surface, and generally conical end sections that do not form a part of the working surface, the balloon further including at least one radiopaque identifier for indicating the relative position of the working surface, said identifier being provided on at least one of the conical end sections of the balloon so as to define the extent of the working surface.

2.2 The catheter of paragraph 2.1, wherein the identifier comprises a marking.

2.3 The catheter of paragraph 2.1 or 2.2, wherein a first marking is provided at a first transition between the first conical section end section and the working surface and a second marking is provided at a second transition between the second end section and the working surface.

2.4 The catheter of paragraph 2.2 or 2.3, wherein the marking comprises a strip.

2.5 The catheter of any of the foregoing paragraphs, wherein the identifier comprises a longitudinal strip extending between an end of the balloon and the barrel section.

2.6 The catheter of any of the foregoing paragraphs, further including a plurality of identifiers.

2.7 The catheter of paragraph 2.6, wherein each of the plurality of identifiers comprises a longitudinally extending strip.

2.8 The catheter of paragraph 2.6 or 2.7, wherein the identifiers comprise annular bands.

2.9 The catheter of paragraph 2.6 or paragraph 2.8 as dependent on paragraph 2.6, wherein the identifiers comprise longitudinally extending strips.

2.10 The catheter of any of the foregoing paragraphs 2.1 to 2.9, wherein at least two spaced radiopaque identifiers are provided on each end section.

2.11 The catheter of any of the foregoing paragraphs 2.1 to 2.10, further including at least one radiopaque identifier on the barrel section.

2.12 The catheter of any of the foregoing paragraphs 2.1 to 2.11, wherein the identifier is a first identifier comprising a first pattern, and further including a second identifier comprising a second, different pattern.

2.13 The catheter of any of the foregoing paragraphs 2.1 to 2.12, wherein the identifier includes at least one letter or number.

2.14 The catheter of any of the foregoing paragraphs 2.1 to 2.13, wherein the identifier comprises a logo.

2.15 The catheter of any of the foregoing paragraphs 2.1 to 2.14, wherein the identifier comprises a scale.

2.16 The catheter of any of the foregoing paragraphs 2.1 to 2.15, further including a drug on the balloon.

3.1 An inflatable balloon for use in connection with a catheter, comprising: an inflatable body including a working surface extending in a longitudinal direction between a first end and a second end, the body having at least one radiopaque identifier provided along the body for identifying at least a first end of the working surface, the radiopaque identifier having a first radiographic quality for identifying the location of the first end of the working surface and a second radiographic quality at a location other than at the first end of the working surface.

3.2 The balloon of paragraph 3.1, wherein the second radiographic quality is provided for identifying the second end of the working surface.

3.3 The catheter of paragraph 3.2, wherein the first radiographic quality and the second radiographic quality are substantially the same.

3.4 The balloon of paragraph 3.1, wherein the radiopaque identifier comprises a marking.

3.5 The balloon of paragraph 3.1, wherein the radiopaque identifier follows a generally helical path from the first end to the second end of the working surface.

3.6 The balloon of paragraph 3.1, wherein the identifier comprises a plurality of helical identifiers extending along the working surface.

3.7 The balloon of paragraph 3.1, wherein the identifier comprises a radiopaque filament.

3.8 The balloon of paragraph 3.7, wherein the filament is wound helically along at least a portion of the working surface of the balloon.

3.9 The balloon of any of the foregoing paragraphs 3.1 to 3.8, further including a drug on the balloon.

3.16 A balloon for use in connection with a catheter, comprising: a body having an outer surface and at least one winding extending along the outer surface of the balloon, said balloon having a radiopaque quality.

3.17 The balloon of paragraph 3.16, wherein the winding comprises a radiopaque filament.

3.18 The balloon of any of the foregoing paragraphs, wherein the radiopaque identifier comprises a helical pattern or a diamond pattern.

3.19 A catheter including the balloon of any of the foregoing paragraphs.

3.20 An inflatable balloon for use in connection with a catheter comprising a radiopaque identifier comprising a helical pattern or a diamond pattern.

4.1 A balloon catheter for use in connection with a guidewire, comprising: an elongated, tubular shaft extending in a longitudinal direction, said shaft having a proximal end and a distal end; an inflatable balloon supported along the distal end of the shaft, the balloon when inflated including first and second spaced ends and a working surface between the ends; and at least one wire including at least a radiopaque portion for identifying the location of working surface of the balloon.

4.2 The catheter of paragraph 4.1, wherein said wire comprises a material having a shape memory for adjusting between a first state and a second state.

4.3 The catheter of paragraph 4.1 or 4.2, wherein the at least one wire extends generally in the longitudinal direction.

4.4 The catheter of any of the foregoing paragraphs 4.1 to 4.3, wherein the radiopaque portion is elongated.

4.5 The catheter of any of the foregoing paragraphs 4.1 to 4.4, wherein the wire at least partially comprises a polymer.

4.6 The catheter of any of the foregoing paragraphs 4.1 to 4.5, wherein the at least one wire is at least partially elastic.

4.7 The catheter of any of the foregoing paragraphs 4.1 to 4.6, comprising: a plurality of wires extending generally in the longitudinal direction, at least one of the wires including at least a radiopaque portion for identifying the location of working surface of the balloon.

4.8 The catheter of any of the foregoing paragraphs 4.1 to 4.7, wherein at least one wire extends along an outer surface of the balloon.

4.9 The catheter of any of the foregoing paragraphs 4.1 to 4.8, wherein at least one wire extends along an inner surface of the balloon.

4.10 The catheter of any of the foregoing paragraphs 4.1 to 4.9, wherein at least one wire extends from the first end to the second end of the balloon.

4.11 The catheter of any of the foregoing paragraphs 4.1 to 4.10, wherein the radiopaque portion of at least one wire extends along a portion of the balloon corresponding to the working surface.

4.12 The catheter of any of the foregoing paragraphs 4.1 to 4.11, wherein the radiopaque portion of at least one wire extends along other than along the portion of the balloon corresponding to the working surface.

4.13 The catheter of paragraph 4.7 or any of paragraphs 4.8 to 4.12 as dependent on paragraph 4.7, wherein the wires are spaced substantially equidistantly around a circumference of the balloon.

4.14 The catheter of any of the foregoing paragraphs 4.1 to 4.13, wherein the wire includes a compliant or semi-compliant portion.

4.15 The catheter of any of the foregoing paragraphs 4.1 to 4.14, wherein at least one end of the at least partially radiopaque wire is attached to a bond connecting the balloon to the shaft.

4.16 The catheter of any of the foregoing paragraphs 4.1 to 4.15, further including a drug provided on the balloon.

4.17 The catheter of any of the foregoing paragraphs 4.1 to 4.16, wherein at least one wire at least partially comprises a material having a shape memory for adjusting between a first state and a second state.

4.18 The catheter of paragraph 4.2 or 4.17, wherein the shape memory material comprises NITINOL.

5.1 A balloon catheter adapted for use with a guidewire, comprising: an elongated, tubular shaft extending in a longitudinal direction, said shaft having a proximal end and a distal end; an inflatable balloon supported along the distal end of the shaft, the balloon when inflated including first and second spaced ends and a working surface between the ends; and an insert located within the interior compartment of the balloon, the insert including at least a radiopaque portion separate from the shaft.

5.2 The catheter of paragraph 5.1, wherein the insert is adapted for moving relative to the shaft.

5.3 The catheter of paragraph 5.1 or 5.2, wherein the insert extends from a first end of the balloon to one end of the working surface.

5.4 The catheter of any of the foregoing paragraphs 5.1 to 5.3, wherein the insert comprises a tube made at least partially of a radiopaque material.

5.5 The catheter of any of the foregoing paragraphs 5.1 to 5.4, wherein the insert comprises at least one finger.

5.6 The catheter of paragraph 5.5, wherein the finger includes a radiopaque end portion.

5.7 The catheter of any of the foregoing paragraphs 5.1 to 5.6, wherein the insert comprises a plurality of fingers adapted for moving from a retracted condition to an expanded condition when the balloon is inflated.

5.8 The catheter of any of the foregoing paragraphs 5.1 to 5.7, further including a retractable sheath at least partially covering the insert.

5.9 The catheter of any of the foregoing paragraphs 5.1 to 5.8, wherein the insert comprises a wire.

5.10 The catheter of paragraph 5.9, wherein the wire includes a radiopaque portion corresponding to the working surface.

5.11 The catheter of paragraph 5.10, wherein the wire extends from the first end to the second end of the balloon, and the radiopaque portion comprises an intermediate portion of the wire.

5.12 The catheter of paragraph 5.10 or 5.11, wherein the wire extends from the first end to the second end of the balloon, and the radiopaque portion comprises an end portion of the wire.

5.13 The catheter of any of the foregoing paragraphs 5.1 to 5.12, wherein at least one end of the insert is connected at a location where the balloon connects to the tubular shaft.

5.14 The catheter of any of the foregoing paragraphs 5.1 to 5.13, wherein the insert comprises an annular band.

5.15 The catheter of any of the foregoing paragraphs 5.1 to 5.14, wherein the insert includes perforations.

5.16 The catheter of any of the foregoing paragraphs 5.1 to 5.15, wherein the insert comprises a material having a shape memory.

5.17 The catheter of any of the foregoing paragraphs 5.1 to 5.16, further including a drug on the balloon.

6.1 A parison for being blow molded into a medical balloon for a catheter, comprising: a first tubular layer having a functional modification; and a second tubular layer adapted for bonding with the first tubular layer to form the blow molded balloon.

6.2 The parison of paragraph 6.1, wherein the first layer is external to the second layer.

6.3 The parison of paragraph 6.1, wherein the first layer is internal to the second layer.

6.4 The parison of any of the foregoing paragraphs, wherein the functional modification comprises a radiopaque strip.

6.5 The parison of paragraph 6.4, wherein the strip comprises a circumferential band.

6.6 The parison of paragraph 6.4 or 6.5, wherein the strip extends between a first end and a second end of the first layer.

6.7 The parison of any of the foregoing paragraphs, wherein the first tubular layer is spaced from the second tubular layer.

6.8 The parison of any of the foregoing paragraphs, wherein the functional modification is selected from the group consisting of an added radiopacifier, a surface pattern, an etching, one or more perforations, and combinations of the foregoing.

6.9 A medical balloon formed by the parison of any of the foregoing paragraphs, comprising: a tubular, inflatable body comprising a wall, the body including first and second generally conical ends and a generally cylindrical barrel section between the generally conical ends and providing a working surface.

6.10 The balloon of paragraph 6.9, wherein the first layer extends from the first end to the second end of the balloon.

6.11 The balloon of paragraph 6.9, wherein the first layer extends along only the working surface.

6.12 The balloon of any of paragraphs 6.9 to 6.11, wherein the first layer extends along an entire circumference of a portion of the wall.

6.13 The balloon of any of paragraphs 6.9 to 6.12, wherein the first layer extends along the full circumference of the wall.

6.14 The balloon of any of paragraphs 6.9 to 6.13, wherein the wall includes first and second spaced shoulders, and wherein the first layer is positioned between the shoulders.

6.15 The balloon of any of paragraphs 6.9 to 6.14, wherein the first and second layers both extend from a first end to a second end of the balloon.

6.16 The balloon of any of paragraphs 6.9 to 6.15, further comprising an at least partially radiopaque tube positioned over the barrel section and extending substantially along the working surface.

6.17 The balloon of paragraph 6.16, further including first and second shoulders adjacent the proximal and distal ends of the radiopaque tube.

6.18 The balloon of paragraph 6.16 or 6.17, wherein the entire tube is radiopaque.

7.1 A balloon catheter, comprising: an elongated, tubular shaft having a proximal end and a distal end; and a balloon positioned along the distal end of the shaft, a portion of a wall of the balloon partially comprising a coextruded radiopaque material.

7.2 The catheter of paragraph 7.1, wherein the radiopaque portion comprises at least one strip extending along a working surface of the balloon.

7.3 The catheter of paragraph 7.1 or 7.2, wherein the radiopaque portion comprises at least one strip extending along a full length surface of the balloon.

7.4 The catheter of any of paragraphs 7.1 to 7.3, wherein the radiopaque portion comprises at least one strip extending along a first cone section of the balloon.

7.5 The catheter of paragraph 7.4, wherein the radiopaque portion comprises at least one strip extending along a second cone section of the balloon.

7.6 The catheter of any of paragraphs 7.1 to 7.5, wherein the balloon includes a plurality of radiopaque portions.

7.7 The catheter of paragraph 7.6, wherein each of the plurality of radiopaque portions comprises a longitudinal strip.

7.8 The catheter of paragraph 7.7, wherein the strips extend at least along a working surface of the balloon.

7.9 The catheter of any of paragraphs 7.6 to 7.8, wherein the plurality of radiopaque portions are spaced apart in a circumferential direction.

7.10 The catheter of any of the foregoing paragraphs 7.1 to 7.9, wherein the balloon includes a barrel section and conical sections at each end of the barrel section, and wherein the radiopaque portion is provided on the barrel section.

7.11 The catheter of any of the foregoing paragraphs 7.1 to 7.10, wherein the balloon includes a barrel section and conical sections at each end of the barrel section, and wherein the radiopaque portion is provided on one or both of the cone sections.

7.12 The catheter of any of the foregoing paragraphs 7.1 to 7.11, wherein the radiopaque portion comprises a layer of the balloon wall.

7.13 The catheter of paragraph 7.12, wherein the layer comprises an inner layer.

7.14 The catheter of paragraph 7.12 or 7.13, wherein the layer comprises an outer layer.

7.15 The catheter of paragraph 7.14, wherein the outer layer is etched.

7.16 The catheter of any of paragraphs 7.12 to 7.15, wherein the balloon includes a barrel section and conical sections at each end of the barrel section, and the layer extends along the entire barrel section.

7.17 The catheter of any of paragraphs 7.12 to 7.16, wherein the balloon includes a barrel section and conical sections at each end of the barrel section, and the layer extends along the entirety of one or both of the conical sections.

7.18 The catheter of any of the foregoing paragraphs 7.1 to 7.17, wherein all portions of the wall comprise coextruded radiopaque material.

7.19 The catheter of any of the foregoing paragraphs 7.1 to 7.18, further including a drug on the balloon.

7.20 The catheter of any of the foregoing paragraphs 7.1 to 7.19, wherein the radiopaque material comprises ePTFE.

8.1 A balloon catheter, comprising: a shaft extending in a longitudinal direction, said shaft having a proximal end and a distal end, and supporting at least one radiopaque identifier; an inflatable balloon supported along the distal end of the shaft, the balloon when inflated including a working surface; and an actuator for aligning at least one end of the working surface with the at least one radiopaque identifier.

8.2 The catheter of paragraph 8.1, wherein the actuator includes a first position corresponding to a deflated state of the balloon and a second position corresponding to the inflated state of the balloon.

8.3 The catheter of paragraph 8.1 or 8.2, wherein the actuator comprises a spring.

8.4 The catheter of any of the foregoing paragraphs 8.1 to 8.3, wherein the spring comprises a leaf spring.

8.5 The catheter of any of the foregoing paragraphs 8.1 to 8.4, wherein the actuator comprises a plurality of springs spaced circumferentially about the catheter.

8.6 The catheter of any of the foregoing paragraphs 8.1 to 8.5, wherein a first portion of the actuator is fixed to the balloon and a second portion of the actuator is adapted for movement relative to the shaft.

8.7 The catheter of paragraph 8.6, wherein the first portion of the actuator is captured between two layers on the wall of the balloon.

8.8 The catheter of paragraph 8.6 or 8.7, wherein the shaft includes a channel for at least partially receiving the second portion of the actuator.

8.9 The catheter of any of the foregoing paragraphs 8.1 to 8.8, further including a stop for stopping the movement of the actuator.

8.10 The catheter of any of the foregoing paragraphs 8.1 to 8.9, wherein the radiopaque identifier comprises a marker attached to the shaft.

8.11 The catheter of any of the foregoing paragraphs 8.1 to 8.10, wherein the radiopaque identifier comprises an insert positioned within the interior compartment of the balloon.

8.12 The catheter of any of the foregoing paragraphs 8.1 to 8.11, wherein the actuator is a first actuator for aligning a distal end of the working surface with the radiopaque identifier, and further including a second actuator for aligning a proximal end of the working surface with the radiopaque identifier.

8.13 The catheter of paragraph 8.12, wherein each of the first and second actuators comprise a plurality of springs.

8.14 The catheter of any of the foregoing paragraphs, wherein the radiopaque identifier comprises a first marking and a second marking, and wherein the actuator is a first actuator for aligning a distal end of the working surface with the first marking, and further including a second actuator for aligning a proximal end of the working surface with the second marking.

8.15 The balloon catheter of any of the foregoing paragraphs 8.1 to 8.14, comprising: a shaft extending in a longitudinal direction, said shaft having a proximal end and a distal end, and supporting first and second radiopaque identifiers; a first actuator for aligning a first end of the working surface with the first radiopaque marking; and a second actuator for aligning a second end of the working surface with the second radiopaque identifier.

8.16 The balloon catheter of any of the foregoing paragraphs 8.1 to 8.15, comprising: a shaft for carrying the balloon, the shaft including at least one channel formed in an outer portion of a wall of the shaft; and an actuator having a first end connected to the balloon and a second end at least partially positioned in the channel.

8.17 The balloon catheter of any of the foregoing paragraphs 8.1 to 8.16, comprising: a shaft for carrying the balloon, the shaft including a plurality of channels formed in an outer portion of the wall of the shaft.

8.18 The catheter of paragraph 8.17, further including an actuator having a first end connected to the balloon and a second end positioned in at least one of the channels.

8.19 The catheter of any of the foregoing paragraphs 8.1 to 8.8, comprising: a spring connected to a wall of the balloon.

8.20 The catheter of paragraph 8.19, wherein the spring is at least partially radiopaque.

8.21 The catheter of paragraph 8.19 or 8.20, wherein the spring is connected to a conical section of the wall of the balloon.

8.22 The balloon catheter of any of the foregoing paragraphs 8.1 to 8.21, wherein the balloon includes a drug.

9.1 A balloon catheter for use with a guidewire, comprising: an elongated, tubular shaft extending in a longitudinal direction, said shaft having a proximal end and a distal end; an inflatable balloon connected to the distal end of the shaft, the balloon including a working surface; a radiopaque identifier for identifying the working surface; and a receiver adjacent the proximal end of the shaft and adapted for allowing the shaft to move relative to the receiver in at least the longitudinal direction.

9.2 The catheter of paragraph 9.1, wherein the shaft carries a stop, and the receiver further includes a recess for receiving the stop, said recess having a dimension in the longitudinal direction that is greater than a corresponding dimension of the stop.

9.3 The catheter of paragraph 9.2, further including a tube for supplying an inflation fluid to inflate the balloon, said tube being connected to the receiver and generally coaxial with the shaft, and wherein the stop forms a seal with the recess to prevent the inflation fluid from passing around the shaft.

9.4 The catheter of paragraph 9.3, wherein the seal comprises an O-ring arranged coaxially with the shaft.

9.5 The catheter of paragraph 9.1, wherein the radiopaque identifier is separate from the shaft.

9.6 The catheter of paragraph 9.5, wherein the radiopaque identifier comprises an insert positioned within the interior compartment of the balloon.

9.7 The catheter of paragraph 9.6, wherein the insert comprises a tubular sleeve arranged coaxially with the shaft.

9.8 The catheter of paragraph 9.6, wherein the insert comprises a first insert at a proximal end of the balloon and a second insert at a distal end of the balloon.

9.9 The catheter of paragraph 9.1, further including a guidewire for positioning in the shaft.

9.10 A hub for a balloon catheter having an elongated, tubular shaft extending in a longitudinal direction, said shaft having a proximal end and a distal end, and an inflatable balloon connected to the distal end of the shaft for being inflated by an inflation fluid, comprising: a body including a receiver for receiving a proximal portion of the shaft and adapted for allowing the shaft to move relative to the receiver in at least the longitudinal direction; and a stop for restraining the movement of the shaft relative to the body in the longitudinal direction.

9.11 The hub of paragraph 9.10, wherein the body includes a guidewire port arranged in communication with the receiver, and further including an inflation port for introducing the inflation fluid for inflating the balloon.

9.12 The hub of paragraph 9.10, wherein the receiver further includes a recess for receiving the stop, said recess having a dimension in the longitudinal direction that is greater than a corresponding dimension of the stop.

9.13 The hub of paragraph 9.12, wherein the stop forms a seal with the recess to prevent the inflation fluid from passing.

9.14 The hub of paragraph 9.10, wherein the stop comprises an O-ring.

9.15 A catheter including a guidewire shaft having a distal end connected to a balloon and at a proximal end mounted for sliding movement.

9.16 The catheter of any of the foregoing paragraphs, further including a drug on the balloon.

9.17 A catheter comprising a hub for receiving a proximal end of a guidewire shaft, the shaft being adapted to slidably move in a restrained manner relative to the hub.

10.1 A balloon catheter, comprising: an elongated tubular shaft having a proximal end and a distal end spaced apart in a longitudinal direction, the shaft along a distal portion including at least one radiopaque identifier, said distal portion being formed of a material resistant to elongation in the longitudinal direction; and an inflatable, non-compliant balloon extending over the distal portion of the shaft.

10.2 The catheter according to paragraph 10.1, wherein the balloon includes a generally cylindrical barrel section positioned between generally conical sections, said barrel section including a working surface having at least one edge aligned with the radiopaque identifier.

10.3 The catheter according to paragraph 10.2, wherein the radiopaque identifier comprises a first marker positioned at the at least one edge of the working surface, and further including a second marker positioned at the opposite edge of the working surface in the longitudinal direction.

10.4 The catheter according to paragraph 10.2, wherein each marker comprises a radiopaque band swaged to the distal portion of the shaft.

10.5 The catheter according to paragraph 10.1, wherein the distal portion of the shaft comprises a tube adapted for guiding a guidewire from a proximal end of the balloon to a distal end of the balloon.

10.6 The catheter according to paragraph 10.1, wherein at least the distal portion of the shaft comprises steel.

10.7 The catheter according to paragraph 10.1, wherein the shaft comprises steel.

10.8 The catheter according to paragraphs 10.6 or 10.7, wherein the steel shaft comprises a stainless steel.

10.9 The catheter according to paragraphs 10.7 or 10.8, wherein the steel shaft includes a spiral cut along a portion other than the distal portion covered by the balloon.

10.10 The catheter according to paragraphs 10.7 or 10.8, wherein the steel shaft comprises a polymer layer.

10.11 The catheter according to paragraph 10.10, wherein the polymer layer comprises an outer layer of the shaft.

10.12 The catheter according to paragraph 10.1, wherein the distal portion of the shaft comprises a polymer shaft including a braid or mesh.

10.13 The catheter according to paragraph 10.1, wherein the balloon includes a generally cylindrical barrel section positioned between generally conical sections, the distal portion of the shaft extending from a first end of a first conical section to a second end of a second conical section.

10.14 The catheter according to paragraph 10.1, wherein the non-compliant balloon comprises one or more inelastic fibers.

10.15 The catheter according to paragraph 10.1, wherein the non-compliant balloon comprises polyethylene terephthalate.

10.16 The catheter of any of the foregoing paragraphs 10.1 to 10.15, further including a drug on the balloon.

11.1 A balloon catheter, comprising: a shaft extending in a longitudinal direction and adapted for expanding from a compressed condition to an expanded condition in the longitudinal direction, the shaft supporting at least one radiopaque identifier; and an inflatable balloon positioned along the shaft, the balloon when inflated including a working surface for aligning with the radiopaque identifier in at least the expanded condition of the shaft.

11.2 The catheter of paragraph 11.1, wherein the expandable shaft comprises a first portion connected in tandem to an expandable element.

11.3 The catheter of paragraphs 11.1 or 11.2, wherein the expandable element comprises a spring.

11.4 The catheter of paragraph 11.3, wherein the spring comprises a coil spring.

11.5 The catheter of paragraphs 11.3 or 11.4, wherein the spring comprises a tension coil spring.

11.6 The catheter of paragraph 11.2, wherein the expandable element comprises a bellows.

11.7 The catheter of paragraph 11.2, wherein the expandable element comprises a fiber matrix.

11.8 The catheter of paragraph 11.7, further including a spring associated with the fiber matrix.

11.9 The catheter of any of paragraphs 11.2-11.8, wherein the expandable element is inside an interior compartment of the balloon.

11.10 The catheter of any of paragraphs 11.2-11.8, wherein the expandable element is outside an interior compartment of the balloon.

11.11 The catheter of any of paragraphs 11.2-11.10, wherein the expandable element connects to one end of the balloon.

11.12 The catheter of any of paragraphs 11.2-11.10, wherein the expandable element connects the first portion of the shaft to a second portion of the shaft.

11.13 The catheter of any of the foregoing paragraphs 11.1 to 11.12, wherein the shaft comprises an inflation lumen for delivering an inflation fluid to the balloon.

11.14 The catheter of any of the foregoing paragraphs 11.1 to 11.13, wherein the expandable shaft in at least a partially expanded condition a port for delivering the inflation fluid to the balloon, said port being closed when the shaft is in a non-expanded condition.

11.15 The catheter of any of the foregoing paragraphs 11.1 to 11.14, wherein the expandable shaft comprises a first expandable element connecting a first portion of the shaft to a second portion of the shaft, and further including a second expandable element connecting the second portion of the shaft to a third portion of the shaft.

11.16 The catheter of paragraph 11.15, wherein the first and second expandable elements comprise first and second coil springs.

11.17 The catheter of paragraph 11.16, wherein the first and second coil springs have different spring constants.

11.18 The catheter of any of the foregoing paragraphs 11.1 to 11.17, wherein the radiopaque identifier comprises a pair of spaced radiopaque markers, one positioned in alignment with a first end of the working surface and another positioned at a second end of the working surface.

11.19 The catheter of any of paragraphs 11.15-11.18, wherein the first and second expandable elements comprise a radiopaque material.

11.20 The catheter of any of the foregoing paragraphs 11.1 to 11.19, wherein the radiopaque identifier comprises a spring.

11.21 The catheter of paragraph 11.2, wherein the expandable element comprises a spring having a variable spring constant.

11.22 The catheter of any of the foregoing paragraphs 11.1 to 11.21, wherein the shaft comprises a guidewire lumen.

11.23 The catheter of any of the foregoing paragraphs 11.1 to 11.22, further including a passage adjacent the tip for receiving a guidewire external to the balloon.

11.24 The catheter of paragraph 11.2, wherein the first portion is adjacent a distal end of the shaft.

11.25 A balloon catheter, comprising: a shaft; a balloon; and an expandable element adapted for expanding in the longitudinal direction connecting the shaft to the balloon.

11.26 The catheter of paragraph 11.25, wherein the expandable element is selected from the group consisting of a spring, a bellows, a fiber matrix, or combinations of the foregoing.

11.27 The catheter of paragraph 11.25 or 26, wherein the expandable element comprises an encapsulated spring.

11.28 A balloon catheter comprising a balloon and an inflation lumen including an expandable element adapted for expanding in the longitudinal direction for providing a fluid to the balloon.

11.29 The catheter of any of paragraphs 11.25-11.28, wherein the expandable element comprises a radiopaque material.

11.30 The catheter of any of the foregoing paragraphs 11.1 to 11.29, further including a drug on the balloon.

12.1 A balloon catheter, comprising: an elongated, tubular shaft extending in a longitudinal direction, said shaft having a proximal end and a distal end; and a balloon having an inflation compartment formed a balloon wall including a working surface, and further including at least one chamber adjacent to the working surface adapted for receiving an identifier for identifying the location of the working surface.

12.2 The balloon catheter of paragraph 12.1, wherein the shaft includes a first lumen for supplying a fluid to the chamber.

12.3 The balloon catheter of paragraph 12.2, wherein the shaft includes a port between the first lumen and the chamber.

12.4 The balloon catheter of paragraph 12.2, wherein the shaft includes a second lumen for supplying a fluid to an interior compartment of the balloon.

12.5 The balloon catheter of paragraph 12.4, wherein the shaft includes a port between the second lumen and the interior compartment.

12.6 The balloon catheter of any of the foregoing paragraphs 12.1 to 12.5, wherein the identifier comprises a contrast agent.

12.7 The balloon catheter of any of the foregoing paragraphs 12.1 to 12.6, wherein the contrast agent comprises a material selected from the group consisting of a radiopacifier, polyvinyl acetate, cellulose, a fluid, a liquid, a solid, a powder, or combinations of the foregoing.

12.8 The balloon catheter of any of the foregoing paragraphs 12.1 to 12.7, wherein the chamber comprises a first chamber at a proximal end of the balloon, and further including a second chamber at a distal end of the balloon.

12.9 The balloon catheter of paragraph 12.8, wherein the second chamber is adapted for receiving the identifier from a lumen in the shaft in fluid communication with the first chamber via a port.

12.10 The balloon catheter of any of the foregoing paragraphs 12.1 to 12.9, wherein the chamber is generally annular.

12.11 The balloon catheter of any of the foregoing paragraphs 12.1 to 12.10, wherein the chamber is positioned between a transition from a barrel section to a conical section of the balloon and an end of the balloon.

12.12 The balloon catheter of any of the foregoing paragraphs 12.1 to 12.11, wherein the chamber is provided by a film attached to the balloon wall.

12.13 The balloon catheter of any of the foregoing paragraphs 12.1 to 12.12, wherein the chamber is embedded in the balloon wall.

12.14 The balloon catheter of any of the foregoing paragraphs 12.1 to 12.13, wherein the chamber is provided by a film extending between the balloon wall and an outer surface of the shaft.

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Accordingly, it is intended that the present invention not be limited to the described embodiments, but that it has the full scope defined by the language of the following claims, and equivalents thereof.

The invention claimed is:

1. A balloon catheter adapted for use with a guidewire, comprising:
   an elongated, tubular shaft extending in a longitudinal direction, said shaft having a proximal end and a distal end;
   an inflatable balloon having an interior compartment extending along the distal end of the shaft, the balloon when inflated including first and second spaced ends and a cylindrical portion including a working surface therebetween; and
   an insert comprising at least one finger located within the interior compartment of the balloon, the insert having a proximal end attached to the balloon, the insert including at least a radiopaque portion at a distal end of the insert for identifying an edge of the working surface,
   wherein the insert extends from the first end of the balloon to align with the edge of the working surface.

2. The catheter of claim 1, wherein the insert comprises a material having a shape memory.

3. The catheter of claim 1, further including a drug on the balloon.

4. A balloon catheter adapted for use with a guidewire, comprising:
   an elongated, tubular shaft extending in a longitudinal direction, said shaft having a proximal end and a distal end;
   an inflatable balloon supported along the distal end of the shaft, the balloon when inflated including first and second spaced ends and a working surface therebetween;
   an insert located within an interior compartment of the balloon and at least partially separate from the shaft, the insert including at least a radiopaque portion for identifying an edge of the working surface, the insert adapted for allowing inflation fluid to pass from the tubular shaft into the interior compartment of the balloon; and
   a retractable sheath in the interior compartment of the balloon for at least partially covering the insert,
   wherein the insert comprises a plurality of fingers adapted for moving from a retracted condition to an expanded condition when the balloon is inflated,
   wherein the plurality of fingers are spaced apart to allow fluid to freely flow past the plurality of fingers into the interior compartment.

5. The catheter of claim 4, wherein the insert comprises a material having a shape memory.

6. The catheter of claim 4, further including a drug on the balloon.

7. A balloon catheter adapted for use with a guidewire, comprising:
   an elongated, tubular shaft extending in a longitudinal direction, said shaft having a proximal end and a distal end;
   an inflatable balloon having an interior compartment extending along the distal end of the shaft, the balloon when inflated including first and second spaced ends and a cylindrical portion including a working surface therebetween; and
   an insert comprising at least one finger located within the interior compartment of the balloon, the insert having a proximal end attached to the balloon, the insert including at least a radiopaque portion at a distal end of the insert for identifying an edge of the working surface, wherein the insert comprises a first insert located in a first conical portion of the balloon at the first end, and the catheter further includes a second insert spaced from the shaft and located in a second conical portion of the balloon at the second end, the first insert aligning with the edge at a proximal end of the working surface and the second insert aligning with a distal end of the working surface.

8. The catheter of claim 7, wherein the insert comprises a material having a shape memory.

9. The catheter of claim 7, further including a drug on the balloon.

* * * * *